United States Patent [19]

Allenmark et al.

[11] Patent Number: 5,080,902

[45] Date of Patent: * Jan. 14, 1992

[54] ARTICLE AND A PROPHYLACTIC COMPOSITION CONTAINING A MICROBICIDE

[75] Inventors: Stig Allenmark, Kullavik; Magnus Lindstedt; Lars Edebo, both of Gothenburg, all of Sweden

[73] Assignee: Berol Kemi AB, Stenungsund, Sweden

[*] Notice: The portion of the term of this patent subsequent to Dec. 13, 2005 has been disclaimed.

[21] Appl. No.: 212,993

[22] Filed: Jun. 29, 1988

Related U.S. Application Data

[63] Continuation-in-part of Ser. No. 948,261, Dec. 31, 1986, Pat. No. 4,790,978.

[30] Foreign Application Priority Data

Jan. 7, 1986 [SE] Sweden .................. 8600046
Jun. 29, 1987 [SE] Sweden .................. 8702674

[51] Int. Cl.$^5$ .................. A61F 6/00; A61K 31/14
[52] U.S. Cl. .................. 424/430; 424/431; 424/432; 424/433; 424/DIG. 14; 514/556; 514/642; 514/841; 514/931; 422/28
[58] Field of Search .................. 128/844; 424/DIG. 14, 424/430–433; 514/556, 642

[56] References Cited

U.S. PATENT DOCUMENTS

| | | | |
|---|---|---|---|
| 2,585,048 | 2/1952 | Shelanski | 167/58 |
| 2,888,383 | 5/1959 | Byrne | 167/93 |
| 2,904,041 | 9/1959 | Brown | 128/844 |
| 3,443,563 | 5/1969 | Ishihama et al. | 128/844 |
| 3,594,468 | 7/1971 | Saurino | 424/430 X |
| 4,321,277 | 3/1982 | Saurino | 424/DIG. 14 |
| 4,446,103 | 5/1984 | Nudel et al. | 422/28 |
| 4,499,077 | 2/1985 | Stockel et al. | 514/642 |
| 4,525,346 | 6/1985 | Stark | 514/642 |
| 4,601,954 | 7/1986 | Coleman | 422/28 |
| 4,790,978 | 12/1988 | Allenmark et al. | 514/642 |

FOREIGN PATENT DOCUMENTS 0190797 8/1986 European Pat. Off. .
1061457 3/1967 United Kingdom .

OTHER PUBLICATIONS

M. Métayer, Ann. Pharm. Franc., 10 (1952), pp. 435–439.
T. Nakamiya et al., "Antibacterial Activity of Lauryl Esters of DL-Lysine", Ferment Tech., vol. 54, No. 6, (1976), pp. 369–373.
A. E. Epsstein et al., "Bactericidial Quaternary Ammonium Salts Derived from Monochloro-Acetate Esters", Khim. Farm. Zh., vol. 14, No. 23, (1980), pp. 292–295.
Khim.-Farm. Zh., vol. 14, No. 5 (1980), pp. 23–26.
Chemical Abstracts, vol. 93 (1980), 113917t (Abs. of Ref. Ar herein).
Nakamiya et al., "Antibacterial Activity . . . ", J. Ferm. Techn., vol. 54, (1976), pp. 369–373.
Bundesverebandder Pharmazeutischeal Industry, "Rote Liste 1977/1978", Preparations Nos. 45125B and 45126B.

Primary Examiner—Thurman K. Page
Assistant Examiner—James M. Spear
Attorney, Agent, or Firm—Spencer & Frank

[57] ABSTRACT

A prophylactic agent for controlling venereal diseases. As an active microbicidal component, the agent has an ammonium compound having hydrolyzable ester group.

6 Claims, No Drawings

ARTICLE AND A PROPHYLACTIC COMPOSITION CONTAINING A MICROBICIDE

CROSS-REFERENCE TO RELATED APPLICATION

This application is a continuation-in-part of Ser. No. 06/948,261 filed Dec. 31st, 1986 which issued as U.S. Pat. No. 4,790,978 on Dec. 13th, 1988.

BACKGROUND OF THE INVENTION

1. Field of the Invention

The present invention refers to a prophylactic agent for controlling venereal diseases, said agent containing, as an active microbicidal component, an ammonium compound having a hydrolyzable ester bond.

2. Description of the Related Art

For a long time it has been known that a number of venereal diseases, such as gonorrhoea and chlamydia, are spread by sexual contact. These diseases are caused by bacteria. In later years also venereal diseases caused by viruses, such as AIDS (Acquired Immune Deficiency Syndrome) and herpes, have gotten increasing attention. For prophylactic purposes, the use of condoms, foams, ointments, gels and other products are recommended onto which have been applied or which contain microbicidal compounds. The microbicidal compounds which have been used, however, have the disadvantage that they cause a persistent irritation after use.

Amphiphilic compounds of the quaternary ammonium type have been long known to exhibit a strong antimicrobial activity; the disclosure by Domagk in 1935 having had great impact on the development of this field. (G. Domagk, Dtsch. Med. Wochenschr. 61, 829 (1935). It has become evident, however, from studies of acute, as well as chronic toxicity, that these compounds may give rise to skin irritation and hypersensitivity, and, therefore, are not recommended for certain applications.

SUMMARY OF THE INVENTION

Therefore, it is an object of this invention to find antimicrobial compounds which do not have the drawback mentioned above. Another object of the invention is to permit a rapid inactivation by a controllable degradation of the antimicrobial compound. Still another object is that the degradation will take place at a pH value from about 6 to about 8.5, which is a pH value that does not give raise to skin irritation and the like. Also, a still further object is to provide a prophylactic agent for controlling venereal diseases caused by bacteria or viruses which contains or has applied onto it one or more antimicrobial compounds which do not exhibit the drawback mentioned above.

It has now been shown that the above objects are met by a prophylactic agent, which contains or has been treated with a long-chain ammonium compound having the general formula

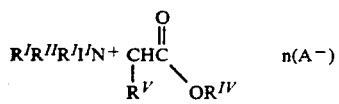
                    I wherein $R^I$, $R^{II}$ and $R^{III}$ are hydrogen or lower alkyl groups, and $R^{IV}$ is a long chain alkyl group having 10 to 18 carbon atoms, $R^V$ is hydrogen or a group having the formula $R^{VI}N^+H_3$, wherein $R^{VI}$ is an alkylene group having 3 to 4 carbon atoms, A is a monovalent counter ion, and n is the number of cationic groups in the compound, and has good activity against microorganisms which cause a number of the most common venereal diseases, such as gonorrhoea and chlamydia. Especially surprising and valuable is the fact that the ammonium compound also has a good effect on viruses which cause venereal diseases. Examples of such viruses are herpes simplex virus, human immunodeficiency virus (AIDS virus), and human papilloma virus. It is thus also possible to control AIDS and herpes.

It is important that the ester bond of the ammonium compound is hydrolyzable at a neutral pH or above. The pH of the vagina is low, however, usually within the range 2–4, and within this range the ammonium compounds are stable and are able to kill bacteria and viruses in the vaginal lumen. At the vaginal wall, however, the pH value increases significantly, and when the ammonium compound contacts the tissues of the wall, its ester bond is hydrolyzed and the ammonium compound is transformed into inactive, harmless products, whereby a residual microbicidal irritation after use of the prophylatic agent of the invention is avoided. This is a very important feature when the compounds are to be used in prophylactic agents against venereal diseases.

The lower alkyl groups $R^I$, $R^{II}$ and $R^{III}$ preferably are alkyl groups having 1–4 carbon atoms, and most preferably they are methyl groups. Preferably $R^{IV}$ is a straight chain alkyl group. The counter ion A is usually a halide ion, such as chloride, or $HSO_4-$.

Examples of lower alkyl groups are methyl, ethyl, propy, isopropyl, butyl, secondary butyl and isobutyl, but ethyl and especially methyl are preferred. The long-chain alkyl group $R^{IV}$ can be decyl, dodecyl, dodecenyl, tetradecyl, hexadecyl, octadecyl, octadecenyl, octadecadienyl and oktadecatrienyl. Among these groups, the saturated groups are especially preferred.

Examples of preferred ammonium compounds are compounds having the formulae

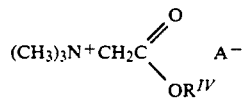
                    II

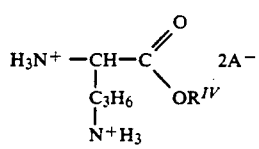
                    III

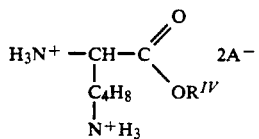
                    IV wherein $R^{IV}$ and A have the meanings stated above.

The ammonium compounds described above have previously been disclosed in the chemical literature (I. Metayer, Ann. pharm. franc. 10, 435, 439 (1952) and they have also been shown to have antibacterial properties (A. E. Epstein et al., Khim. Farm. Zh. 14, 23 (1980) and Teruaki Nakamiya et al., Ferment. Technol. Vol. 54 nr. 6, p. 369–376 (1976). None of these reports discloses, however, that the ammonium compounds in question have a microbicidal effect against bacteria and viruses which cause venereal diseases. Also, there is no disclosure that the compounds hydrolyze rapidly at pH values of about 6 to 8.5, forming non-irritating hydrolysis products.

When an antimicrobial agent is used at appropriate concentration levels, the time needed for full antimicrobial effect is generally fairly short. In most practical situations, the antimicrobial agent is also administrated in a very large excess. Therefore, in many applications the toxic compound is active for a long time after it has exerted its antimicrobial action, which is both undesirable and unnecessary. The invention discloses a principle, according to which the antimicrobial compound loses its biological activity and toxic action by a hydrolytic reaction. The rate of hydrolysis can be regulated by small changes of pH and electrolyte concentration leading to harmless end products within the physiologically suitable pH range of from about 6 to about 8.5.

The solubility of the esters in polar organic solvents, such as lower alcohols, and alcohol/water mixtures is of the order 1 g/ml. Such formulations are highly stable and allow long-term storage.

The esters are highly active against a broad spectrum of Gram positive, as well as Gram negative, bacteria and examples of test data are given below. An important and quite unexpected feature of the invention is also that the compounds have a pronounced effect on viruses which cause venereal diseases.

The temporary disinfecting effect of the esters may be used in hygienic products, such as diapers, tampons, masks, napkins, and cosmetic powders. It may also be employed as disinfectants in, e.g., bubble baths, swimming pools, mouthwashes; and for treatment of packages, food etc. The esters can be applied on webs and garments by dipping into or spraying thereon a slightly acid, aqueous solution of the ester, followed by a rapid drying. Cellulosic fibers may be impregnated by adding the esters to the cellulose pulp slurry in the head-box. When used in dry form, the esters may have the form of a tablet, for example, an effervescent tablet. In an important application of the invention, the esters are applied to or incorporated into prophylactic agents for preventing the spreading of venereal diseases.

The esters may be prepared according to conventional methods by reacting a chloro- or bromoacetyl halide with an alcohol in a halogenated hydrocarbon to provide an alkyl chloro- or bromoacetate. This ester is then converted into the ester of a betaine by reaction with gaseous trialkyalamine in a solvent, such as acetone or toluene.

The ammonium compounds can, in a way known per se, be mixed into or applied to agents for controlling the spread of venereal diseases. Such agents can be sprays, ointments, gels, foams, condoms and vaginal pads. As the ammonium compounds are hydrolyzed at neutral and basic pH, they are usually added in the form of an acidic aqueous solution or alternatively, as a solution based on an organic solvent. When the prophylatic agent is a condom or vaginal pad, the ammonium compound is applied by dipping the prophylatic agent in or spraying it thereon as a solution containing the ammonium compound and subsequent drying. If the prophylatic agent is aqueous, its pH value should be lower than 5.

The prophylatic agent according to the invention would be useful for preventing the spread of various venereal diseases not just among human beings, but among mammals in general who are subject to such diseases. Further, the prophylactic agent according to the invention may be topically applied to the genitals of males or females of the mammal to be protected and, moreover, may be topically applied to any appropriate bodily portion of the mammal through which the microbes may enter the host, such as to mucous membranes.

DESCRIPTION OF THE PREFERRED EMBODIMENTS

The invention is further illustrated by the following examples.

EXAMPLE 1

The bactericidal effect of three esters having the following formula

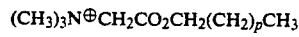

$(CH_3)_3N^{\oplus}CH_2CO_2CH_2(CH_2)_pCH_3$ where p was 10, 12 and 14 respectively, were determined and compared with cetyltrimetylammonium bromide (CTAB), a well-known bactericide. The effect was measured as the concentration needed for reducing the number of viable bacteria by a factor of $10^5$ using $E.$ $coli$ (NCTC 10418) as the test organism during a 5 minute contact time. The results are shown in the Table below.

TABLE 1

| Compound p | Concentration ppm |
|---|---|
| 10 | 50 |
| 12 | 12.5 |
| 14 | >100 |
| CTAB | 12.5 |

From these results it is evident that the material tested have appropriate bactericidal effect.

EXAMPLE 2

The activity towards a series of microorganisms was determined for the compound in Example 1 having 14 carbon atoms all together in its alkyl chain (p=12). Relevant test data are given in the Table below. The activity is expressed as log (cfu/ml) at a 12.5 ppm level and a 5 min contact time in phosphate buffered saline at room temperature. Effects are related to a control (without bactericide) and to CTAB. G+ and G− denote Gram positive and Gram negative species, respectively.

TABLE 2

| | log (cfu/mol) | | |
|---|---|---|---|
| Microorganisms (Type) | control | betaine ester | CTAB |
| Bacillus megaterium (G+) | 6.7 | <3.3 | <3.3 |
| E. Coli (G−) | 7.0 | <3.3 | <3.3 |
| Candida albicans (yeast) | 6.2 | 6.2 | 5.7 |
| Pseudomonas aeruginosa (G−) | 7.4 | 7.5 | 7.5 |
| Staphylococcus aureus (G+) | 5.8 | <3.3 | <3.3 |
| Salmonella typhimurium (G−) | 5.5 | 3.9 | 3.8 |

The effects of the betaine ester and of CTAB are the same within experimental error. Except against the more resistant Ps. aeruginosa and the yeast C. albicans, high activities are found even at these low concentrations.

EXAMPLE 3

The rate of alkaline hydrolysis of the present esters of betaines was determined for the compound in example 1 having 14 carbon atoms in its alkyl chain all together (p=12). The conditions during the test and results obtained are given in the Table below.

TABLE 3

Hydrolysis (given in %) at various pH values and reaction times at 30° C.

| time hrs | 2.6 | 3 | 4 | 5 | 6 | 7 | 8 | 9 |
|---|---|---|---|---|---|---|---|---|
| 0.25 | | | | | | | | 96 |
| 0.5 | | | | | | | 12 | 100 |
| 1 | | | | | | 5 | 60 | 100 |
| 1.5 | | | | | | | 87 | |
| 2 | | | | | | 2 | 10 | |
| 3 | | | | | | | 100 | |
| 4 | | | | | | | 37 | 100 |
| 8 | <1 | <1 | 1 | | | | 80 | |
| 18 | | | | | | 16 | | |
| 20 | | | | | | | 98 | |
| 24 | <1 | 2 | 3 | 5 | | | | |
| 46 | | | | | | 85 | | |
| 48 | <1 | 2 | 5 | 10 | | | | |
| 120 | | | | | | | | |
| 144 | 1 | 6 | 12 | 22 | | | | |

The rate of hydrolysis is also temperature dependent. Upon a temperature increase from 25° C. to 30° C. the half-life at pH 7.0 is decreased from 9 to 5 hrs.

EXAMPLE 4

The rate of hydrolysis and, thereby, the duration of the biological activity of the esters can also be regulated according to this invention by the salt concentration of the medium. The rate of hydrolysis is decreased considerably by an increase in sodium chloride concentration. In the Table below, the effect of sodium chloride on hydrolysis of the compound in Example 2 at a pH 7.9 and 30° C. is shown.

TABLE 4

| | Hydrolysis, % Molarity of NaCl | | | |
|---|---|---|---|---|
| t, hrs | 0 | 0.1 | 0.5 | 1.0 |
| 1 | 51 | 9 | 6 | 2 |
| 2 | 95 | 56 | 9 | 4 |
| 5 | 100 | 100 | 28 | 12 |
| 48 | | | 95 | 77 |

EXAMPLE 5

A solution of 150 ppm of the compound in Example 1 in 10 mM phsophate buffer, pH 8.0, was analyzed at different points in time with respect to degree of hydrolysis, as well as bactericidal effect against E. coli (NCTC 10418). The degree of hydrolysis was determined by analysis of the liberated 1-tetradecanol by gas chromatography (packed 4 ft glass column with 3% SP-2100 on 80/100 Supelcoport; isotermally at 130° C.). The 1-tetradecanol was isolated by careful extraction with hexane. Internal standardization was carried out by means of 1-hexadecanol. Bactericidal effect was determined by dilution of a 1 ml sample to 25 ppm with 5 ml of a sterile buffer, followed by addition of 60 μl of the bacterial suspension. After 5 min at room temperature, a 100-fold dilution and spreading on an agar plate using a Spiral Plater system was performed. The plates were incubated at 37° C. for 20 hrs and counted. Data from the experiments are given in the Table below.

TABLE 5

Hydrolysis and the effect on the bacterial activity.

| Time, min | Hydrolysis, % | Viable counts, cfu/ml (control: 7.1 × 10$^6$) |
|---|---|---|
| 5 | | 0 |
| 23 | 3 | |
| 30 | | 4.1 × 10$^3$ |
| 64 | 25 | |
| 109 | | 3.0 × 10$^6$ |
| 118 | 55 | |
| 149 | 86 | |
| 158 | | 7.9 × 10$^6$ |
| 179 | 89 | |
| 199 | | 7.8 × 10$^6$ |
| 217 | 100 | |
| 238 | 100 | |

EXAMPLE 6

The effect of the following ammonium compounds on gonococci at a concentration of 30 ppm in an 0.01M citrate solution with a pH value of 6 was determined after 1 and 10 minutes. The following results were obtained.

| Compound | Gonococci log cfu/ml | | |
|---|---|---|---|
| | 0 min | 1 min | 10 min |
| $(CH_3)_3NCH_2COOC_{14}H_{29}\ Cl^-$ | 10$^6$ | <10$^1$ | <10$^1$ |
| $(CH_3)_3NCH_2COOC_{16}H_{33}\ Cl^-$ | 10$^6$ | <10$^1$ | <10$^1$ |
| $(NH_3C_4H_8)CHCOOC_{16}H_{33}\ 2Cl^-$ \| $NH_3$ | 10$^6$ | <10$^3$ | <10$^1$ |

EXAMPLE 7

The effect of $(CH_3)_3\ NCH_2COOC_{14}H_{29}\ Cl^-$ in an 0.01M citrate solution on herpes simplex virus was examined. The concentration of the ammonium compound was 20 ppm. After 10 minutes, the concentration of virus had been reduced by a factor greater than 10$^3$.

The present disclosure relates to the subject matter disclosed in Swedish Patent Application No. 8600046-0 filed Jan. 7th, 1986 and Swedish Patent Application No. 8702674-6, filed June 29th, 1987, the entire specifications of which are incorporated herein by reference.

It will be understood that the above description of the present invention is susceptible to various modifications, changes and adaptations, and the same are intended to be comprehended within the meaning and range of equivalents of the appended claims.

What is claimed is:

1. The process of preventing the spread of gonorrhea and chlamydia among mammals, comprising:
   applying an article topically to an appropriate bodily portion of a mammal, the article being a hygienic product comprised of a prophylactic composition containing at least one microbicide in an amount effective for controlling at least one of gonorrhea and chlamydia, which at least one microbicide is hydrolyzable at a pH value ranging from about 6 to about 8.5 and is an ammonium compound having the general formula

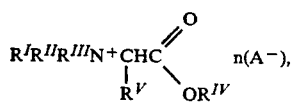

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

2. The process of preventing the spread of herpes and AIDS among mammals, comprising:

applying an article topically to an appropriate bodily portion of a mammal, the article being a hygienic product comprised of a prophylactic composition containing at least one microbicide in an amount effective for controlling at least one of herpes and AIDS, which at least one microbicide is hydrolyzable at a pH ranging from about 6 to about 8.5 and is an ammonium compound having the general formula

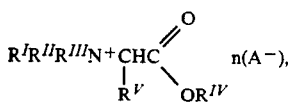

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

3. The process of preventing the spread of gonorrhea and chlamydia among mammals, comprising:

applying a prophylactic composition topically to an appropriate bodily portion of a mammal, the prophylactic composition being comprised of at least one microbicide present in an amount effective for controlling at least one of gonorrhea and chlamydia, which at least one microbicide is hydrolyzable at a pH value ranging from about 6 to about 8.5 and is an ammonium compound having the general formula

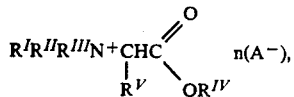

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

4. The process of preventing the spread of herpes and AIDs among mammals, comprising:

applying a prophylactic composition topically to an appropriate bodily portion of a mammal, the prophylactic composition being comprised of at least one microbicide present in an amount effective for controlling at least one of herpes and AIDS, which at least one microbicide is hydrolyzable at a pH ranging from about 6 to about 8.5 and is an ammonium compound having the general formula

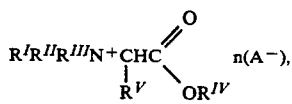

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

5. The process of preventing the spread of gonorrhea, chlamydia, herpes and AIDS among mammals, comprising:

applying an article topically to an appropriate bodily portion of a mammal, the article being a hygienic product selected from the group consisting of a condom, vaginal pad, tampon, napkin, mask and diaper, and being comprised of a prophylactic composition containing at least one microbicide in an amount effective for controlling at least one of gonorrhea, chlamydia, herpes and AIDS, which at least one microbicide is hydrolyzable at a pH value ranging from about 6 to about 8.5 and is an ammonium compound having the general formula

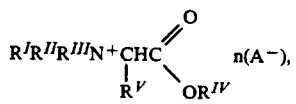

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

6. The process of preventing the spread of gonorrhea, chlamydia, herpes and AIDS among mammals, comprising:

applying a prophylactic composition topically to an appropriate bodily portion of a mammal, the prophylactic composition being comprised of at least on microbicide present in an amount effective for controlling at least one of gonorrhea, chlamydia, herpes and AIDS, and having a form selected from the group consisting of a spray, ointment, foam, gel, tablet, powder and solution, which at least one microbicide is hydrolyzable at a pH value ranging from about 6 to about 8.5 and is an ammonium compound having the general formula

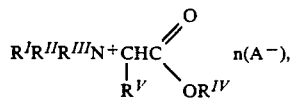

wherein $R^I$, $R^{II}$ and $R^{III}$ are hydrogen or lower alkyl groups having 1 to 4 carbon atoms, $R^{IV}$ is a long chain alkyl group having 10 to 18 carbon atoms, $R^V$ is hydrogen or a group having the formula $R^{VI}N^+H_3$, $R^{VI}$ is an alkylene group having 3 to 4 carbon atoms, A is a monovalent counter ion, and n is the number of cationic groups in the ammonium compound; and allowing the ammonium compound to be hydrolyzed by exposure to a pH ranging from about 6 to about 8.5.

* * * * *